United States Patent
Gill et al.

(10) Patent No.: US 10,363,049 B2
(45) Date of Patent: Jul. 30, 2019

(54) CRANIAL DRILL SYSTEM

(71) Applicant: RENISHAW PLC, Gloucestershire (GB)

(72) Inventors: Steven Streatfield Gill, Bristol (GB); Catriona Anita Fennelly, Dublin (IE)

(73) Assignee: RENISHAW PLC, Wotton-Under-Edge (GB)

( * ) Notice: Subject to any disclaimer, the term of this patent is extended or adjusted under 35 U.S.C. 154(b) by 403 days.

(21) Appl. No.: 14/403,862

(22) PCT Filed: May 31, 2013

(86) PCT No.: PCT/GB2013/051451
§ 371 (c)(1),
(2) Date: Nov. 25, 2014

(87) PCT Pub. No.: WO2013/179053
PCT Pub. Date: Dec. 5, 2013

(65) Prior Publication Data
US 2015/0127040 A1    May 7, 2015

(30) Foreign Application Priority Data
Jun. 1, 2012  (GB) .................................. 1209772.1

(51) Int. Cl.
*A61B 17/16*    (2006.01)
*A61B 17/17*    (2006.01)
*A61B 90/00*    (2016.01)

(52) U.S. Cl.
CPC ...... *A61B 17/1695* (2013.01); *A61B 17/1739* (2013.01); *A61B 17/1617* (2013.01);
(Continued)

(58) Field of Classification Search
CPC .... A61B 17/17; A61B 17/171; A61B 17/1695
See application file for complete search history.

(56) References Cited

U.S. PATENT DOCUMENTS 4,362,161 A   12/1982  Reimels et al.
4,600,006 A    7/1986  Baker
(Continued)

FOREIGN PATENT DOCUMENTS

CN    2054305 U    3/1990
CN    1056818 A   12/1991
(Continued)

OTHER PUBLICATIONS

Feb. 29, 2016 Office Action issued in European Patent Application No. 13 728 239.8.
(Continued)

*Primary Examiner* — Anh T Dang
(74) *Attorney, Agent, or Firm* — Oliff PLC

(57) ABSTRACT

The invention concerns a cranial drill system comprising one or more surgical drill elements for drilling into the brain. The invention also concerns a cranial drilling system comprising a surgical drill element for drilling into the skull and an element for penetrating the dura. The surgical drill element may comprise a profile that forms an opening in the skull having a narrower diameter portion and a wider diameter portion and the piercing element may be arranged to be a close fit in the narrower diameter portion of the opening. The invention also concerns a cranial drill system comprising a guiding element to be located in a hole formed through the skull and a piercing element for piercing the dura. The guiding element may have a passageway or channel therein for receiving the piercing element such that the piercing element is movable relative to the guide element to pierce the dura.

10 Claims, 14 Drawing Sheets

(52) U.S. Cl.
CPC ..... *A61B 17/1637* (2013.01); *A61B 2090/034* (2016.02); *A61B 2090/036* (2016.02); *A61B 2090/062* (2016.02)

(56) References Cited

U.S. PATENT DOCUMENTS

| | | | |
|---|---|---|---|
| 4,830,001 A | | 5/1989 | Walus |
| 4,903,707 A | * | 2/1990 | Knute .................... A61B 5/031 600/561 |
| 5,382,250 A | * | 1/1995 | Kraus ................ A61B 17/1695 408/202 |
| 6,117,143 A | * | 9/2000 | Hynes .................... A61B 90/11 600/429 |
| 6,328,748 B1 | | 12/2001 | Hennig |
| 6,609,020 B2 | | 8/2003 | Gill |
| 8,152,809 B1 | | 4/2012 | Kao et al. |
| 2005/0203526 A1 | | 9/2005 | Ellis |
| 2007/0093841 A1 | | 4/2007 | Hoogland |
| 2008/0294166 A1 | | 11/2008 | Goldin et al. |
| 2009/0024129 A1 | | 1/2009 | Gordon et al. |
| 2010/0034605 A1 | | 2/2010 | Huckins et al. |

FOREIGN PATENT DOCUMENTS

| | | |
|---|---|---|
| CN | 2557082 Y | 6/2003 |
| CN | 201389051 Y | 1/2010 |
| CN | 201389060 Y | 1/2010 |
| CN | 101883535 A | 11/2010 |
| EP | 1 402 843 A1 | 3/2004 |
| EP | 1509153 B1 | 1/2007 |
| GB | 2357700 A | 7/2001 |
| JP | 2010-540202 A | 12/2010 |
| SU | 608525 A1 | 5/1978 |
| WO | 2009047494 A1 | 4/2009 |
| WO | 2011110874 A1 | 9/2011 |

OTHER PUBLICATIONS

Oct. 1, 2013 Search Report issued in International Patent Application No. PCT/GB2013/051451.
Feb. 3, 2017 Office Action issued in Japanese Patent Application No. 2015-514593.
May 15, 2018 Partial European Search Report issued in European Patent Application No. 17202504.1.
Jul. 27, 2018 Office Action issued in Japanese Patent Application No. 2015-514593.
Oct. 29, 2018 Office Action issued in Chinese Patent Application No. 201710141828.2.
Aug. 29, 2018 Extended European Search Report issued in European Patent Application No. 17202504.1.
May 5, 2016 Office Action issued in Chinese Patent Application No. 201380035765.2.

* cited by examiner

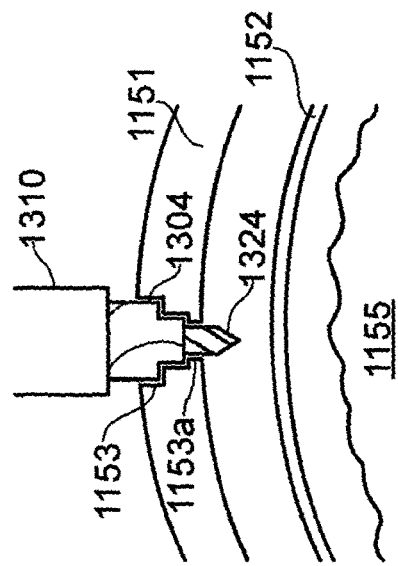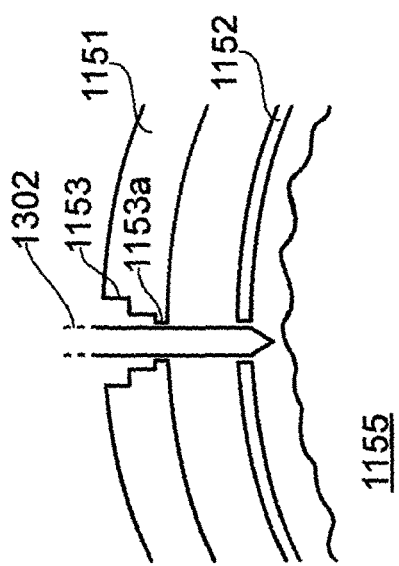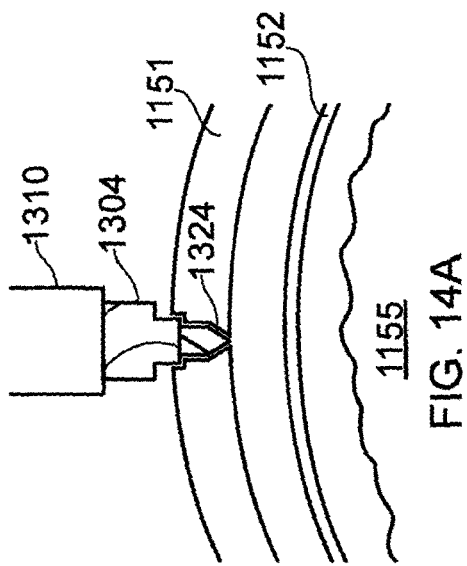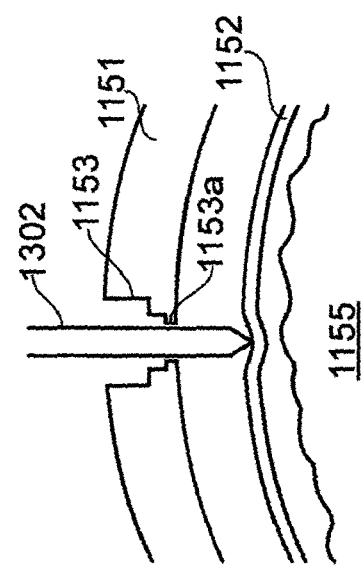

CRANIAL DRILL SYSTEM

FIELD OF INVENTION

This invention concerns a cranial drill system and a method of forming an opening in the skull and the brain. The invention has particular application to a cranial drill system for forming an opening in the skull suitable for receiving a cranial port, such as a cranial port connected with a device, such as a guide device, catheter or electrode.

BACKGROUND

There are many situations where there is a requirement to deliver therapeutic agents to specific targets within the brain parenchyma via implanted catheters. Furthermore, many of these therapeutic agents will cause unwanted side effects if delivered to healthy parts of the brain. Examples of treating abnormalities of brain function include the acute infusion of Gamma-amino-buturic-acid agonists into an epileptic focus or pathway to block transmission, and the chronic delivery of opiates or other analgesics to the peri-aqueductal grey matter or to thalamic targets for the treatment of intractable pain. Also, cytotoxic agents can be delivered directly into a brain tumour. Intraparenchymal infusion can also be used to deliver therapeutic agents to brain targets that cannot be delivered systemically because they will not cross the blood-brain barrier. For example, the treatment of patients with Parkinson's disease, Alzheimer's disease, head injury, stroke and multiple sclerosis may be carried out by the infusion of neurotrophic factors to protect and repair failing or damaged nerve cells. Neurotrophins may also be infused to support neural grafts transplanted into damaged or malfunctioning areas of the brain in order to restore function.

It is also known to insert instruments other than catheters, such as electrodes, directly in the brain parenchyma. For example, stimulating and lesioning electrodes are used in a variety of surgical procedures, including deep brain stimulation (DBS) electrodes. A surgeon wishing to stimulate or lesion a particular area of nervous tissue can target the end of an electrode to the target site so that a desired electrical current can be delivered.

The above described methods rely on targeting the required site as accurately as possible. Slight misplacement of the instrument being inserted may lead to significant morbidity or treatment failure. For example, brain targets for treating functional disorders are usually deeply situated and have small volumes. A desired target for treating Parkinson's disease is situated in the sub-thalamic nucleus and is 3-4 mm in diameter, or an ovoid of 3-4 mm in diameter and 5-6 mm in length. Other targets such as the globus palladus or targets in the thalamus are usually no more than 1-2 mm larger. For such a small target sub-optimal placement of as little as 1 mm will not only reduce the effectiveness of the treatment, but may also induce unwanted side effects such as weakness, altered sensation, worsened speech and double vision. It is also desirable to minimise trauma in certain regions of the brain; for example, the mesencephalon (which includes the subthalamic nucleus, the substantia nigra and the pedunculor-pontine nucleus) is a critical region of the brain where is it is important to minimise trauma from the passage of an electrode or catheter.

A variety of stereotactic devices and methods have thus been developed previously in an attempt to allow instruments to be accurately guided towards a target identified by a surgeon (e.g. using x-rays or magnetic resonance imaging) with the minimum of trauma to other regions of the brain. Examples of prior systems are given in EP1509153, U.S. Pat. Nos. 6,609,020 and 6,328,748.

GB2357700 discloses a guide device comprising a port (head) which is secured in a hole formed in the skull with a tube of the guide device extending into the brain. In order to insert the guide device into the skull a hole is first drilled into the skull under the guidance of a stereotactic frame. Often, the port has a larger diameter than the catheter/electrode/guide tube to be inserted into the brain. Therefore, it is desirable to drill an opening having a stepped form with an enlarged diameter portion for receiving the port. Devices for drilling such a stepped form are known, for example as described in WO2011/110874.

To insert the guide device to the desired target the dura is perforated. The surgeon may do this with a scalpel or a device such as described in WO2009/047494.

Use of a scalpel or a spike, such as disclosed in WO2011/110874, to puncture the dura and the later insertion of probes, such as guide rods, guide tubes, catheters, in to the brain, especially through the denser parts of the brain, may result in the brain being displaced from its original position, resulting in the probes missing the target.

Furthermore, during formation of the openings in the skull and in the dura using these separate instruments, the openings may not be correctly located relative to each other. This is even the case if a stereotactic frame is used for positioning the instruments during formation of the openings as play in the stereotactic frame can result in errors in positioning. This may hinder insertion of an implantable instrument, such as a catheter with integrated port.

SUMMARY OF INVENTION

According to a first aspect of the invention there is provided a cranial drill system comprising one or more surgical drill elements for drilling into the brain.

Drilling out an opening in the brain may reduce the extent to which the brain is pushed away during penetration of the dura and during later insertion of probes, such as guide rods, guide tubes, catheters, electrodes etc, in to the brain. This may result in more accurate placement of the probes/implantable instruments.

The system may comprise first and second drill elements arranged to cooperate together to define a relative position of openings formed using the first and second drill elements. The openings may include an opening in the skull and an opening in the brain. The drill elements may be arranged such that the openings are formed substantially concentric to each other.

The cranial drilling system may comprise a first drilling element for drilling into the brain and a second drilling element for drilling into the skull, the second drilling element having at least a portion with a diameter greater than a diameter of the first drill element. In this way, the drilling system can be used both for drilling an opening into the brain and for drilling an opening into the skull for holding an implantable instrument.

The first drill element and second drill element may be connected or connectable such that drilling with one of the first and second drilling elements is guided by its connection to the other of the second and first drilling elements. Such an arrangement may aid the correct location of the opening in the skull relative to the opening in the brain.

The first drill element may extend from a distal end of the second drill element such that the first drill element has to be drilled into the skull before the second drill element can be drilled in to the skull. In such an arrangement, the second drilling element can be guided into position relative to an opening formed using the first drilling element by its connection with the first drilling element. Drilling using both the first and second elements may be achieved through rotation of a common shaft and in a continuous process and in this sense comprises a "single step" process. In this way, the opening into the brain and the larger diameter opening in the skull can be drilled without having to remove/detach one of the drill elements from the skull/brain. Drilling multiple features in a continuous manner may reduce leakage of cerebrospinal fluid (CSF) due to the accelerated nature of creating the features.

The first drill element and the second drill element may be connected such that a length that the first drill element extends from the distal end of the second drill element can be varied. In this way, the system can be adapted for the specified target.

The first drill element may be connected or connectable to the second drill element such that drilling into the brain with the first drill element is guided by its connection with the second drill element. To achieve this, the second drill element may have a passageway therethrough for receiving the first drill element, the first drill element movable in the passageway from a retracted position, in which the first drill element does not project from a distal end of the second drill element, and an extended position, in which the first drill element does extend from a distal end of the second drill element. In such an arrangement, the first drilling element can be guided into position relative to an opening formed using the second drilling element by its connection with the second drilling element. Such an arrangement may allow the release of cerebrospinal fluid (CSF) from penetrating the dura to be delayed until after the larger diameter opening has been formed in the skull using the second drill element.

The second drilling element for drilling into the skull may comprises a profile that forms an opening in the skull having a narrower diameter portion and a wider diameter portion, The first drilling element may be arranged to be a close fit in the narrower diameter portion of the opening. In one embodiment, the second drilling element comprises a pilot drill element that extends from a distal end of the second drill element, the first drill element arranged to be a close fit in a pilot hole formed using the pilot drill element. In this way, drilling with the first drill element can be guided by fitting the first drill element in the pilot hole.

The second drill element may comprise a profile to form an opening in the skull with one, two or more stepped transitions between the narrower and wider diameter portions. In this way, the opening can support a correspondingly shaped part of an implantable instrument, such as a port of a catheter or guide tube.

The second drilling element may comprise a guide, which, during drilling with the second element, can extend into and is a close fit in an opening formed by the first drilling element.

The cranial drill system may comprise a mount for connecting the first and/or second drill elements to a coordinate positioning apparatus, such as a stereotactic frame and/or robot.

The first drill element may have a length sufficient to extend into the pia mater of the brain. The first drill element may have a length of greater than 10 mm. In this way, the drill element may have sufficient length to reach targets in the brain. The drill element may comprise a twist drill, which may comprise two flutes.

A point angle of a tip of the first drill element may be less than 90°, less than 80°, less than 70° and preferably about 60°. It is believed that a sharp tip will aid penetration of the skull and dura reducing the chances of deflection of the drill element from the skull and dura surfaces and reducing deflections of the brain.

The drill element may be made of a bio-inert material, such as stainless steel or titanium.

According to a second aspect of the invention there is provided a kit including a cranial drill system according to the first aspect of the invention and an implantable instrument for locating within an opening in a skull formed using the cranial drill system, the second drill element arranged to form an opening having a profile corresponding to a profile of the implantable instrument.

According to a third aspect of the invention there is provided neurosurgical apparatus comprising a coordinate positioning apparatus for positioning surgical instruments relative to the skull and a cranial drill system according to the first aspect of the invention.

The coordinate positioning apparatus may be a stereotactic frame or a robot.

According to a fourth aspect of the invention there is provided a method of surgery comprising drilling into a patient's brain.

The method may comprise imaging the patient, identifying targets from the image and drilling into the brain based upon the identified targets.

The method may comprise drilling an opening into the skull using a cranial drill element and, with the cranial drill element remaining in the skull, drilling into the brain using a further drill element, the further drill element connected with the cranial drill element to constrain positioning of the further drill element relative to the cranial drill element.

The method may comprise using a cranial drill element to drill a pilot hole and an opening with a greater diameter than the pilot hole in the skull and then using a further drill element to drill into the brain, the further drill element inserted through the pilot hole. The method may comprise, before drilling into the brain, puncturing the dura with a spike through the pilot hole.

According to a fifth aspect of the invention there is provided a cranial drilling system comprising a surgical drill element for drilling into the skull, the surgical drill element comprising a profile that forms an opening in the skull having a narrower diameter portion and a wider diameter portion, and an element for penetrating the dura, the element arranged to be a close fit, such as an interference fit, in the narrower diameter portion of the opening. The element may be a further drill element or a spike having a substantially smooth outer surface, without flutes of a drill. In one embodiment, the drilling system comprises a spike for puncturing the dura and a further drill element for drilling into the brain.

According to a sixth aspect of the invention there is provided a cranial drill system comprising a guiding element to be located in a hole formed through the skull and a piercing element for piercing the dura, the guiding element having a passageway or channel therein for receiving the piercing element such that the piercing element is movable relative to the guide element to pierce the dura.

In this way, the guide element through its interface with the skull provides a means for positioning the piercing element relative to the hole formed in the skull such that the dura can be pierced at a desired location relative to the hole in the skull.

The guiding element may comprise a dill element for drilling the hole through the skull. Accordingly, the drill is first used to form the hole through the skull and is then used as a guide for guiding the piercing element used to pierce the dura.

Alternatively, the guide element may be a separate element to a drill element used to form the hole. In such an embodiment, the drill element used to drill the hole in the skull is removed from the hole and the separate guide element inserted into the hole and located through its engagement with the hole. To achieve the desired location, the drill element may comprise a profile that forms an opening in the skull having a narrower diameter portion and a wider diameter portion and the guide element may comprise a profile corresponding to the profile of the drill element.

The piercing element may be movable in the passageway or channel from a retracted position in which the piercing element does not project from a distal end of the guide element and an extended position in which the piercing element does extend from a distal end of the guide element. The piercing element may be held within the guide element during location of the guide element in the skull or may be insertable into the passageway or channel after the guide element has been located in the skull. For example, the passageway or channel may extend through the guide element such that the piercing element can be inserted into a proximal end portion of the guide element and moved through the passageway or channel to project from the distal end of the guide element.

The piercing element may be a spike having a substantially smooth outer surface. Alternatively, the piercing element may be a drill element.

DESCRIPTION OF THE DRAWINGS

FIGS. 14A to 14D shows schematically a method of neurosurgery using the cranial drill system shown in FIG. 13;

DESCRIPTION OF EMBODIMENTS

Figure 1:
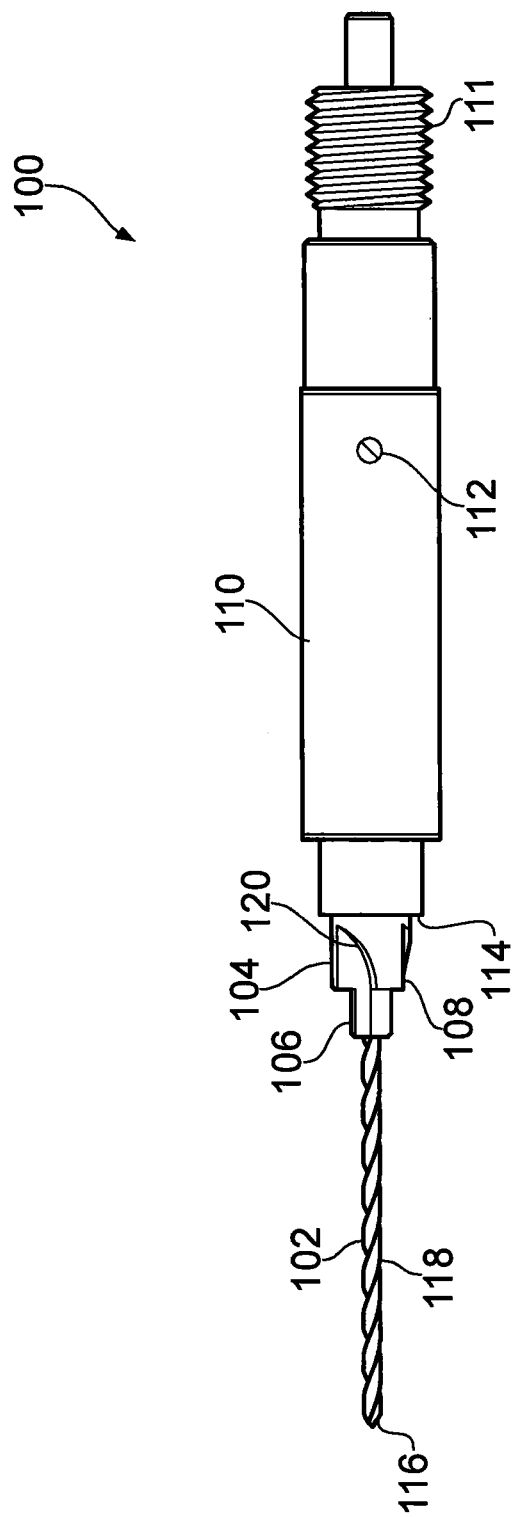
FIG. 1 shows a cranial drill system according to a first embodiment of the invention.

Referring to FIG. 1, a cranial drill system 100 is shown comprising a first drill element 102 for drilling into the brain and a second drilling element 104 for drilling into the skull.

The second drill element 104 has a stepped profile with a first, distal portion 106 having a narrower diameter than a second, proximal portion 108. The second portion 108 also has a diameter greater than a diameter of the first drill element 102. The stepped profile of the second drill element 104 matches that of an implantable instrument to be implanted, such as a port and a catheter to be inserted in the brain.

Figure 9:
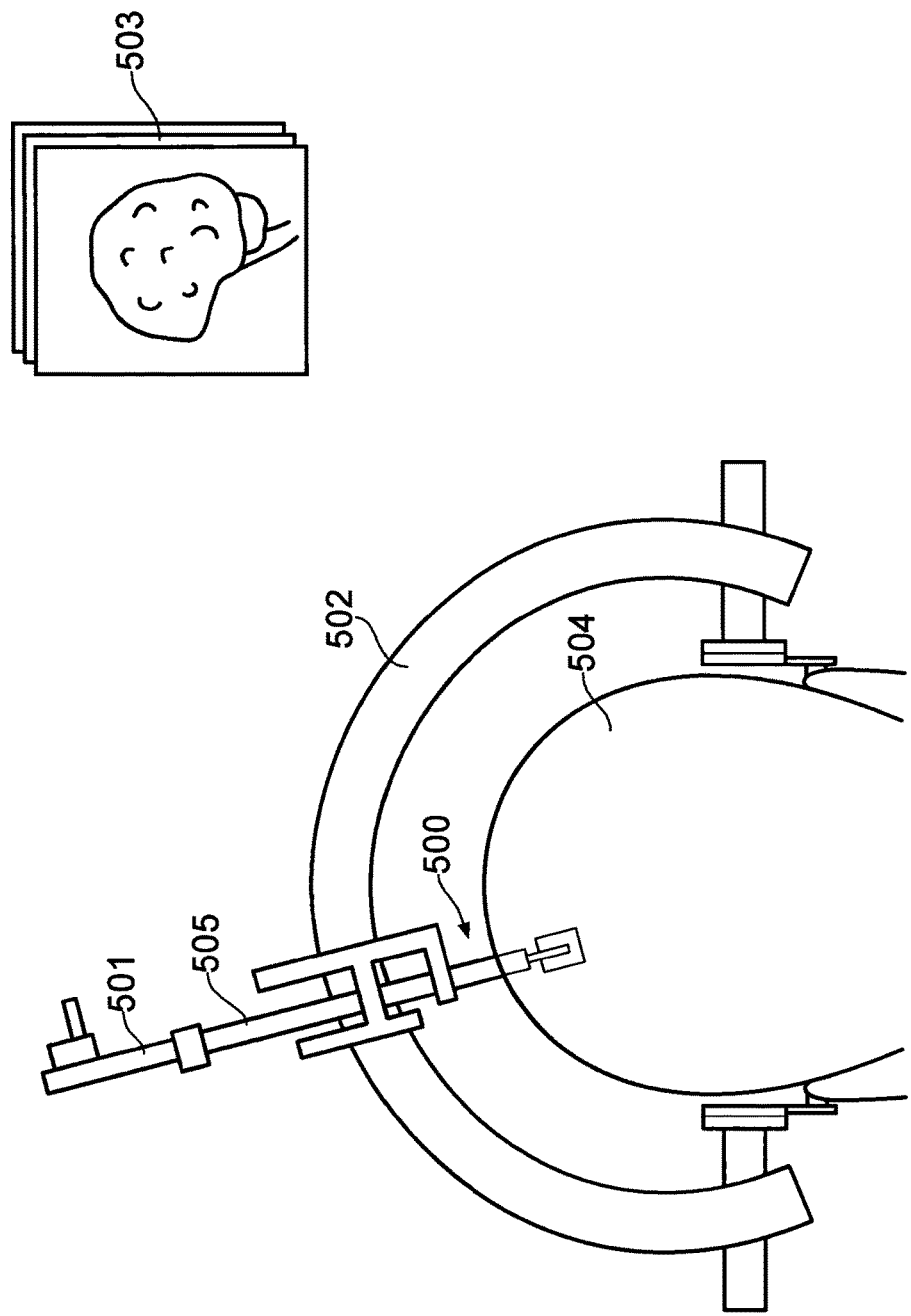
FIG. 9 is a schematic view of a cranial drill system according to the invention attached to a stereotactic frame.

The drill elements 102 and 104 are connected aligned along a common axis to a common shaft 110, which has a mount, in this embodiment a screw thread 111, for attaching the drill system 100 to a surgical drill (501 in FIG. 9). Typically, this is achieved by attaching the drill system 100 to a rod 505 that is carried by a stereoguide frame 502 through which drive from the surgical drill 501 can be transmitted. However, the drill system 100 may also be attached to a robot end effector, which, as well as positioning the drill system, may provide rotation for drilling.

In this embodiment, the first drill element 102 extends into a passageway (not shown) through the second drill element 104 and shaft 110 and is fixed in place by a grub screw 112. However, it will be understood that other fixing devices could be used to secure the first drill element 102 in place. Releasing the first drill element 102 from the grub screw 112 allows the length that the first drill element 102 extends from a distal end of the second drill element 104 to be varied as appropriate for the intended target in the brain.

An interface 114 between the second drill element 104 and the shaft 110 provides an abutment that, in use, can be engaged with the surface of the skull to limit the depth to which the drilling system is inserted into the brain.

The first drill element 102 is a twist drill of stainless steel having a point angle at a tip 116 of about 60°. In this embodiment, a single flute 118 is shown. However, it will be understood that the twist drill may comprise multiple flutes, such as two flutes.

The second drill element 104 also comprises one or more flutes 118 for cutting into the skull.

Figure 2A:
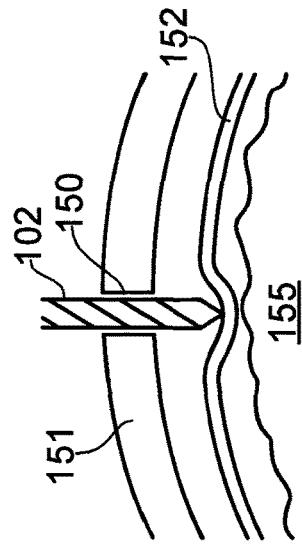
FIGS. 2A to 2D shows schematically a method of neurosurgery using the cranial drill system shown in FIG. 1.
Figure 2B:
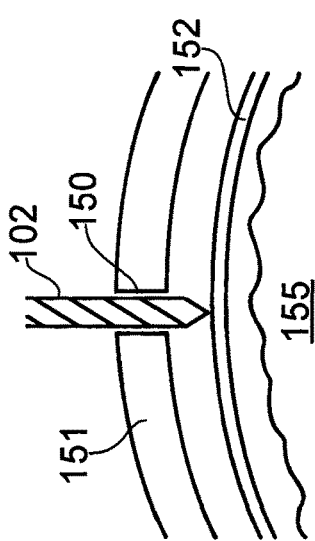
Figure 2C:
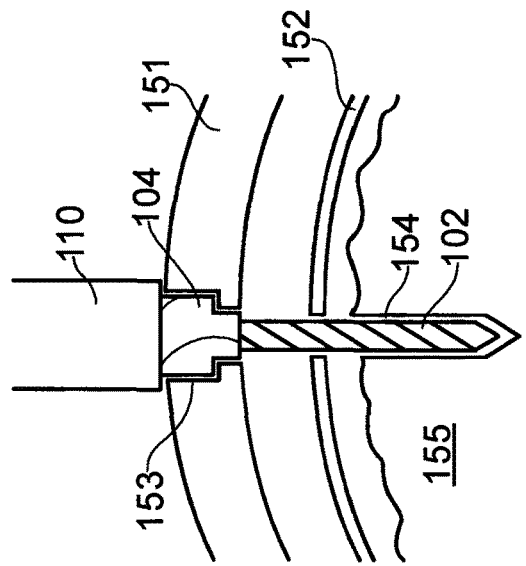
Figure 2D:
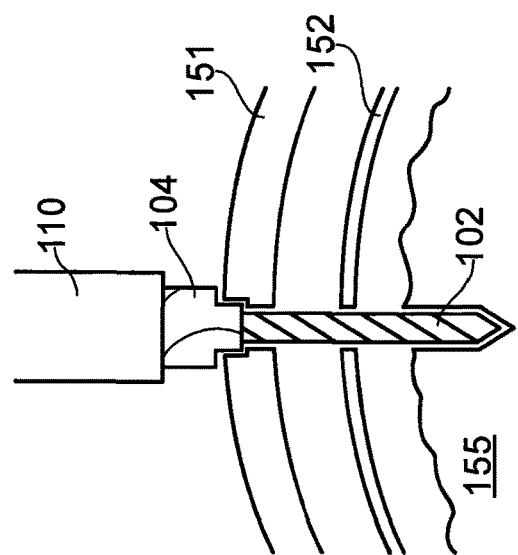

In use, first a target that is to be treated is identified in the brain. This may be achieved by imaging the brain, such as with a CT scan, and identifying from the images 503 a location in the brain to be treated. Based on a measured distance to the target site from a location identified on the skull through which the drill system is to be inserted, a length of the first drill element 102 is set. Referring now to FIGS. 2A to 2D, the drill system 100 allows drilling of the opening through the skull and into the brain in a continuous (one-step) process. Firstly an opening 150 is drilled into the skull 151 using the first drill element 102 positioned as desired using the stereotactic frame 502 or robot. As the drill system is gradually inserted into the head of the patient, the first drill element 102 contacts the dura 152. At first the dura may be slightly deflected as shown in FIG. 2B by the first drill element 102 but the sharp 60° tip 116 soon penetrates the dura. As insertion of the drill system continues with the first drill element 102 entering the brain 155, the second drill element 104 is guided into contact with the skull by virtue of its connection to the first drill element 102 to begin drilling an opening having a larger diameter than that drilled in the skull by the first drill element 102. This is shown in FIG. 2C. Drilling is continued until the abutment 114 engages with the surface of the skull. At this point the first drill element 102 should have reached the intended location in the brain 155 based on its set length and the measurements from the images.

The drilling system 100 is removed and a catheter 600 (shown in FIG. 10) or other implantable instrument can be inserted onto the opening 154 in the brain 155 for delivering the treatment, such as a drug or electronic stimulus. The instrument may comprise a port 601 or plug at its proximal end having a profile corresponding to the opening 153 formed using the second drill element 104. This port or plug is inserted into the opening 153 on insertion of the instrument into the brain.

Figure 3:
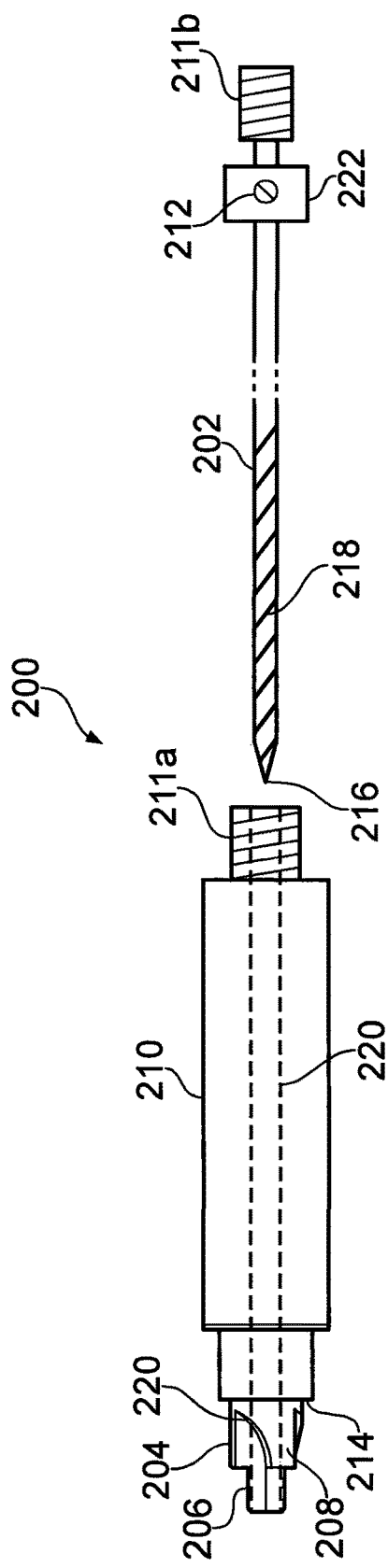
FIG. 3 shows a cranial drill system according to a second embodiment of the invention.

Referring now to FIG. 3, a cranial drilling system 200 according to another embodiment of the invention comprises a first drill element 202 for drilling into the brain and a second drilling element 204 for drilling into the skull. The two drilling elements are similar to the drilling elements described with reference to FIG. 1 and like reference numerals but in the series 200 have been used to refer to corresponding parts.

In this embodiment, the first drilling element 202 can be inserted from the rear of the body 210 through a passageway 220 and pushed though the passageway so as the tip 216 projects from the distal end of drilling element 204. A stop 222 is provided on a shaft of the first drilling element 202 to contact a proximal end of the body 210, limiting the length of the first drilling element 202 that can project from the distal end of the second drilling element 204. A position of the stop 222 on the first drilling element 202 can be adjusted by loosening grub screw 212 and sliding the stop along the first drilling element 202. Separate mounts 211a and 211b are provided on each of the body 210 and the first drilling element 202 for connecting each to a drill.

Figure 4A:
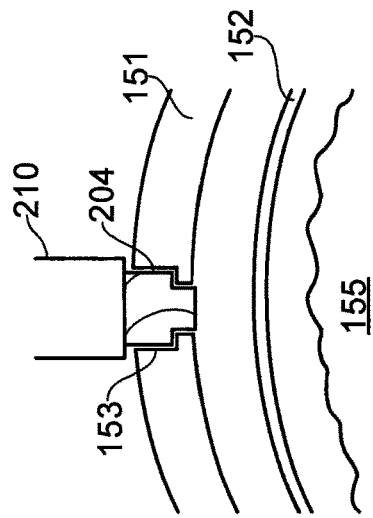
FIGS. 4A to 4D shows schematically a method of neurosurgery using the cranial drill system shown in FIG. 3.
Figure 4B:
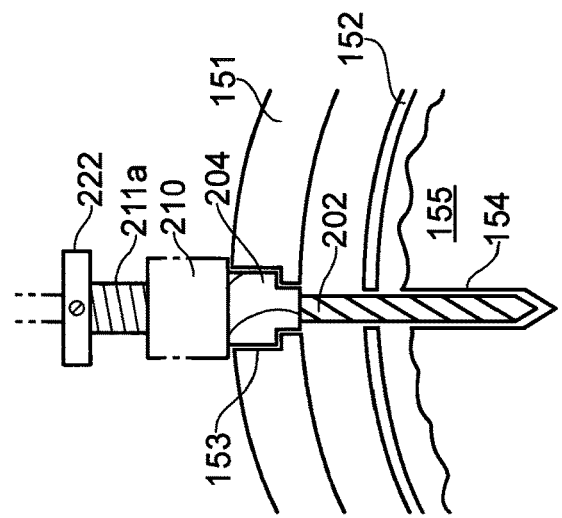
Figure 4C:
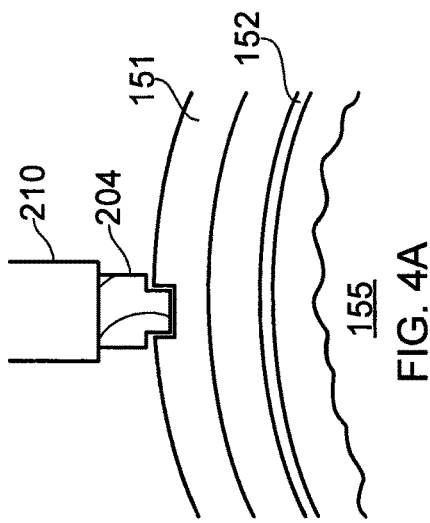
Figure 4D:
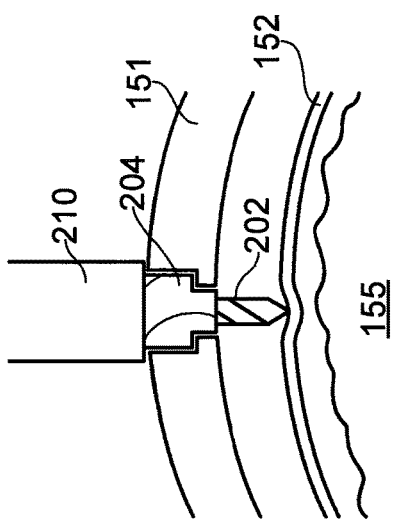

Now referring to FIGS. 4A to 4D, in use, a target is identified from images 503 and the stop 222 moved to a position on the first drilling element 202 such that, when fully inserted into the body 210, the first drilling element projects a desired distance into the brain 155. An opening 153 is then drilled into the skull 151 using the second drilling element (FIGS. 4A and 4B). The first drilling element 102 is connected to the drill and inserted into the passageway 220 so as to project from the second drilling element 204, which remains attached to the skull 151. The first drilling element 202 is used to puncture the dura 152 and drill into the brain 155 (FIGS. 14C and 4D), its position guided by the passageway 220 through the second drilling element 204. Drilling continues until stop 222 engages to proximal end of the body 210.

Once the opening 154 into the brain 155 has been formed an instrument, such as catheter 600, is implanted into the opening 154.

Figure 5:
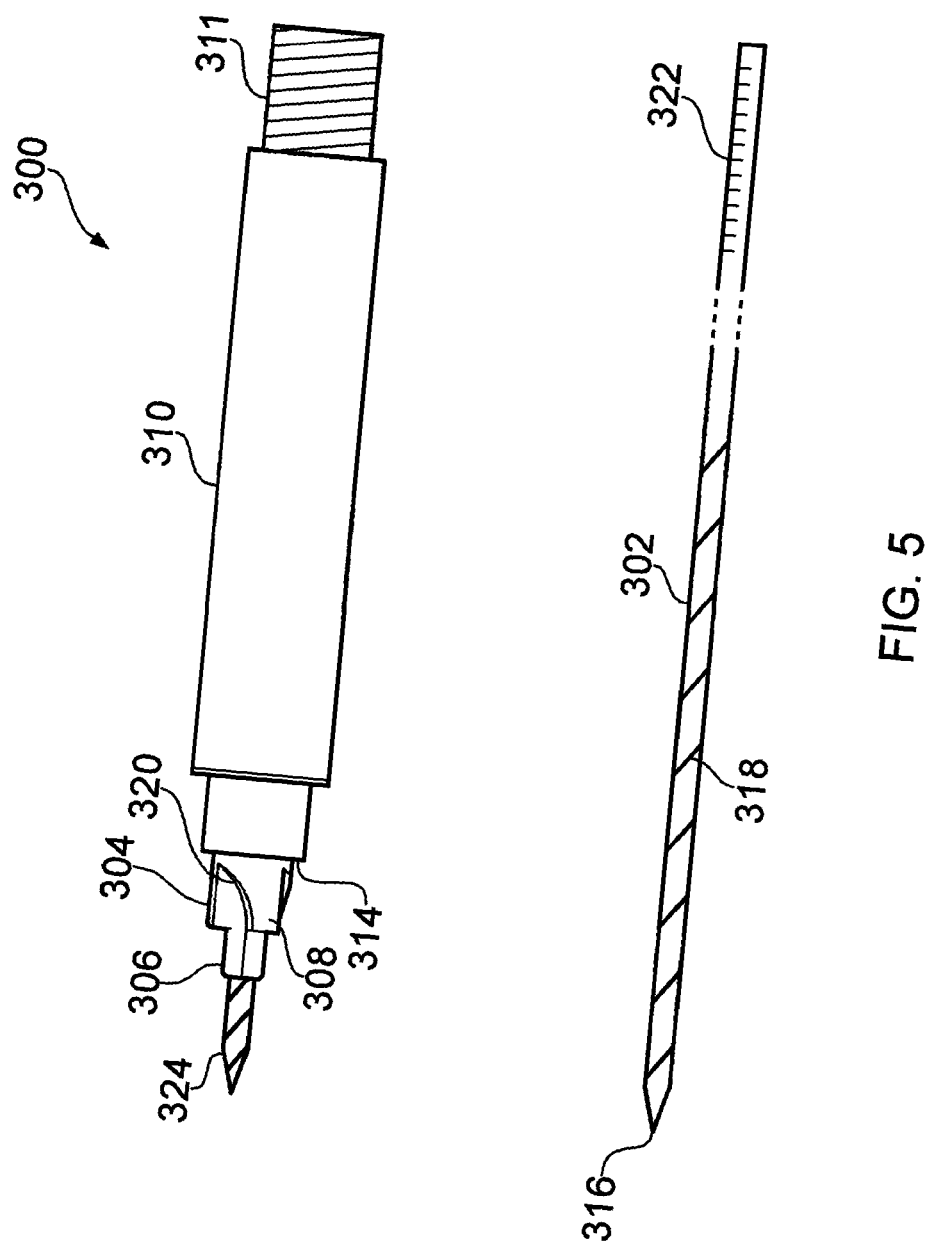
FIG. 5 shows a cranial drill system according to a third embodiment of the invention.
Figure 6A:
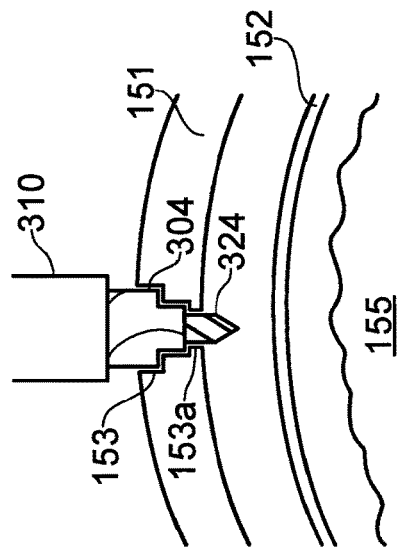
FIGS. 6A to 6D shows schematically a method of neurosurgery using the cranial drill system shown in FIG. 5.
Figure 6B:
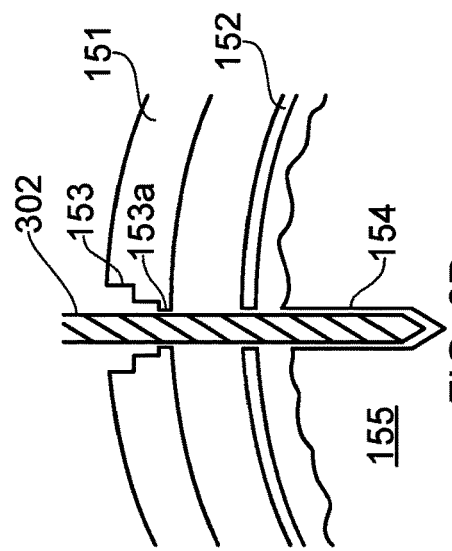
Figure 6C:
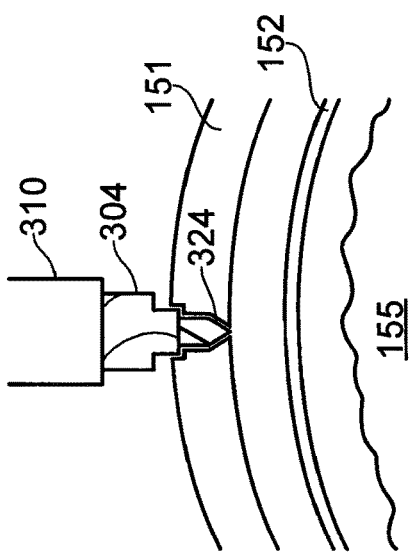
Figure 6D:
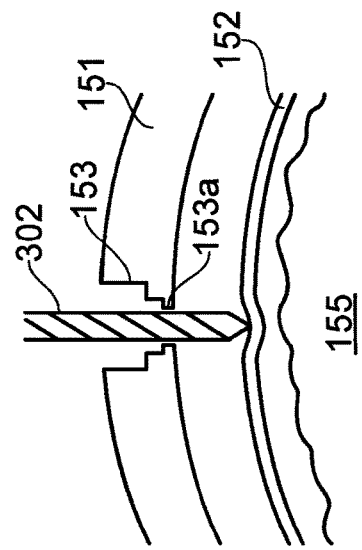

In the embodiment shown in FIG. 5, the drilling system 300 comprises a first drill element 302 for drilling into the brain and a second drilling element 304 for drilling into the skull. The two drilling elements 302, 304 are similar to the drilling elements described with reference to FIGS. 1 and 3 and like reference numerals but in the series 300 have been used to refer to corresponding parts. However, unlike the previous embodiments, the drilling system comprises two instruments that are to be used without a physical connection/engagement.

The first drilling element 302 comprises a distal end having one or more flutes 318 for drilling an opening into the brain 155 and, at a proximal end, scale 322 for measuring the depth that the drill 302 has been inserted into the brain.

The second drilling element 304 comprises at its distal end a pilot drill 324 having a diameter substantially the same as the first drilling element 302.

In use, the second drilling element is first used to drill an opening 153 into the skull 151. This opening 153 includes a pilot hole 153a for guiding later insertion of the first drilling element 302. Once opening 153 has been drilled, the second drilling element is removed and the first drilling element 302 inserted into the opening 153. Contact of the first drilling element 302 with side walls of opening 153a guides the first drilling element 302 to the desired location for penetrating the dura 152 and entering the brain 155. The surgeon can identify whether the target has been reached from the measurement scale 322 on the first drilling element 302.

Figure 7:
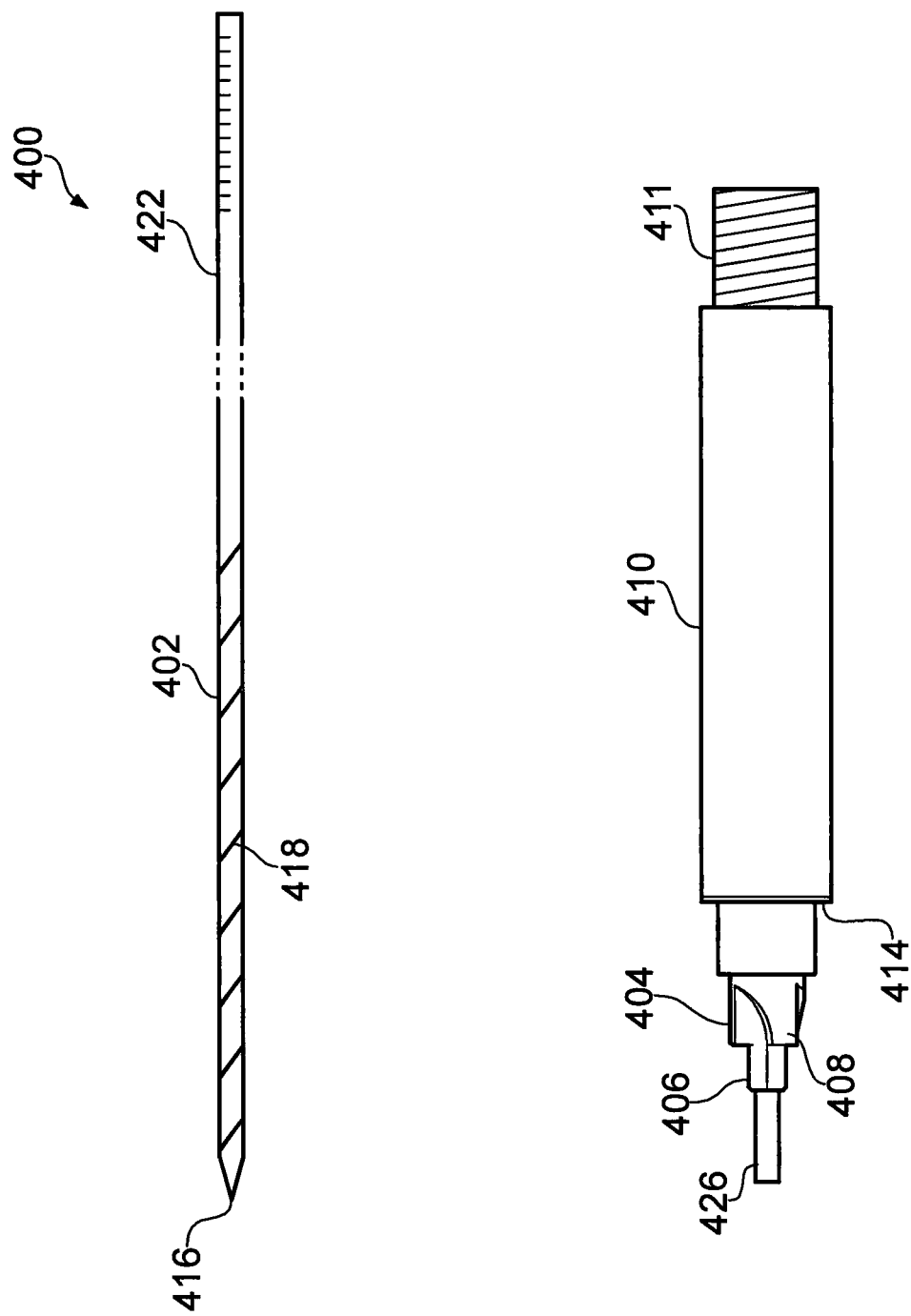
FIG. 7 shows a cranial drill system according to a fourth embodiment of the invention.
Figure 8A:
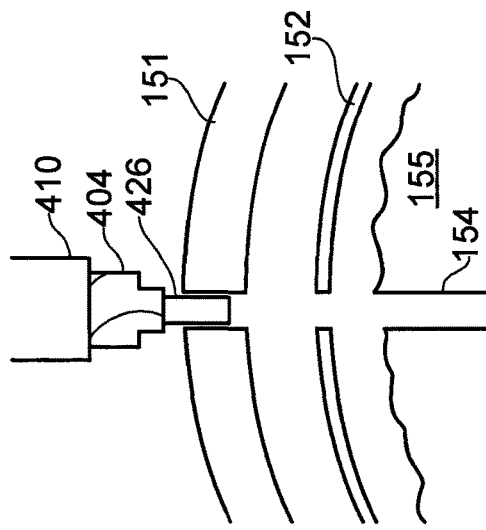
FIGS. 8A to 8B shows schematically a method of neurosurgery using the cranial drill system shown in FIG. 7.
Figure 8B:
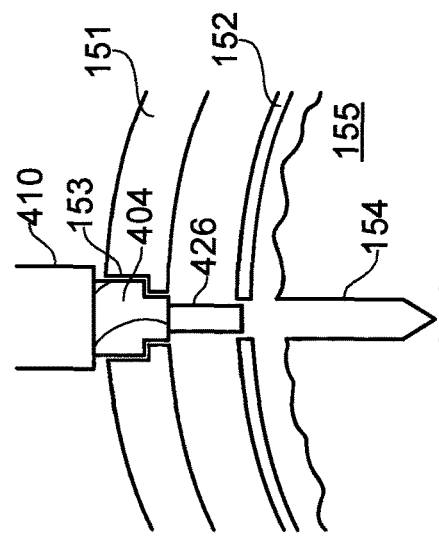
Figure 8C:
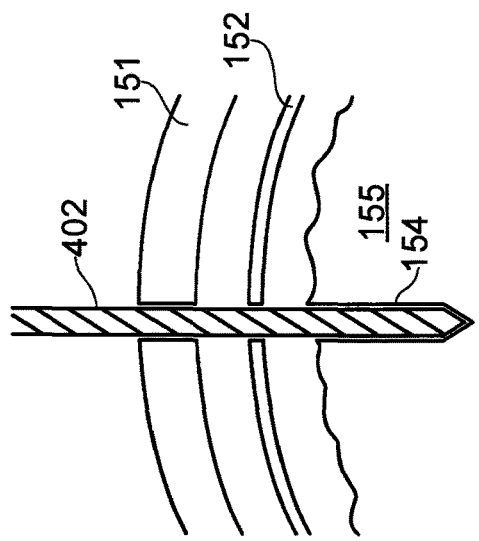
Figure 8D:
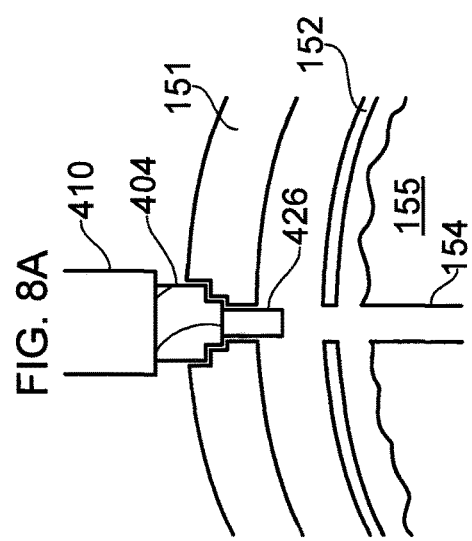

A further embodiment shown in FIG. 7 shows a cranial drilling system 400 comprising a first drill element 402 for drilling into the brain and a second drilling element 404 for drilling into the skull. The two drilling elements 402, 404 are similar to the drilling elements described with reference to FIGS. 1, 3 and 5 and like reference numerals but in the series 400 have been used to refer to corresponding parts. Like the embodiment shown in FIG. 5, the drilling system comprises two instruments that are to be used without a physical connection/engagement.

The first drilling element 402 comprises a distal end having one or more flutes 418 for drilling an opening into the brain 155 and, at a proximal end, scale 422 for measuring the depth that the drill 402 has been inserted into the brain.

The second drilling element 404 comprises at its distal end a guide 426 having a diameter substantially the same as the first drilling element 402.

In use, the first drilling element 402 is first used to drill an opening into the skull 151, to puncture the dura 152 and drill an opening 154 into the brain. The surgeon can identify whether the target has been reached from the measurement scale 422 on the first drilling element 402. The first drilling element 402 is then removed and guide 426 of the second drilling element 404 is inserted into the opening in the skull to locate the second drilling element 404 relative to the opening 154. The second drilling element 404 is then used to drill profiled opening 153, insertion of the drilling element 404 guided by contact of the guide 426 with the side walls of the opening formed previously with the first guide element 402.

FIG. 9 shows a typical set-up a neurological apparatus comprising a stereotactic frame 502 used to position a cranial drilling system 500 on a patient's skull 504. A drill 501 is shown connected to the drilling system 500. The drilling system 500 may be any one of the systems described above with reference to FIGS. 1 to 8.

Figure 10:
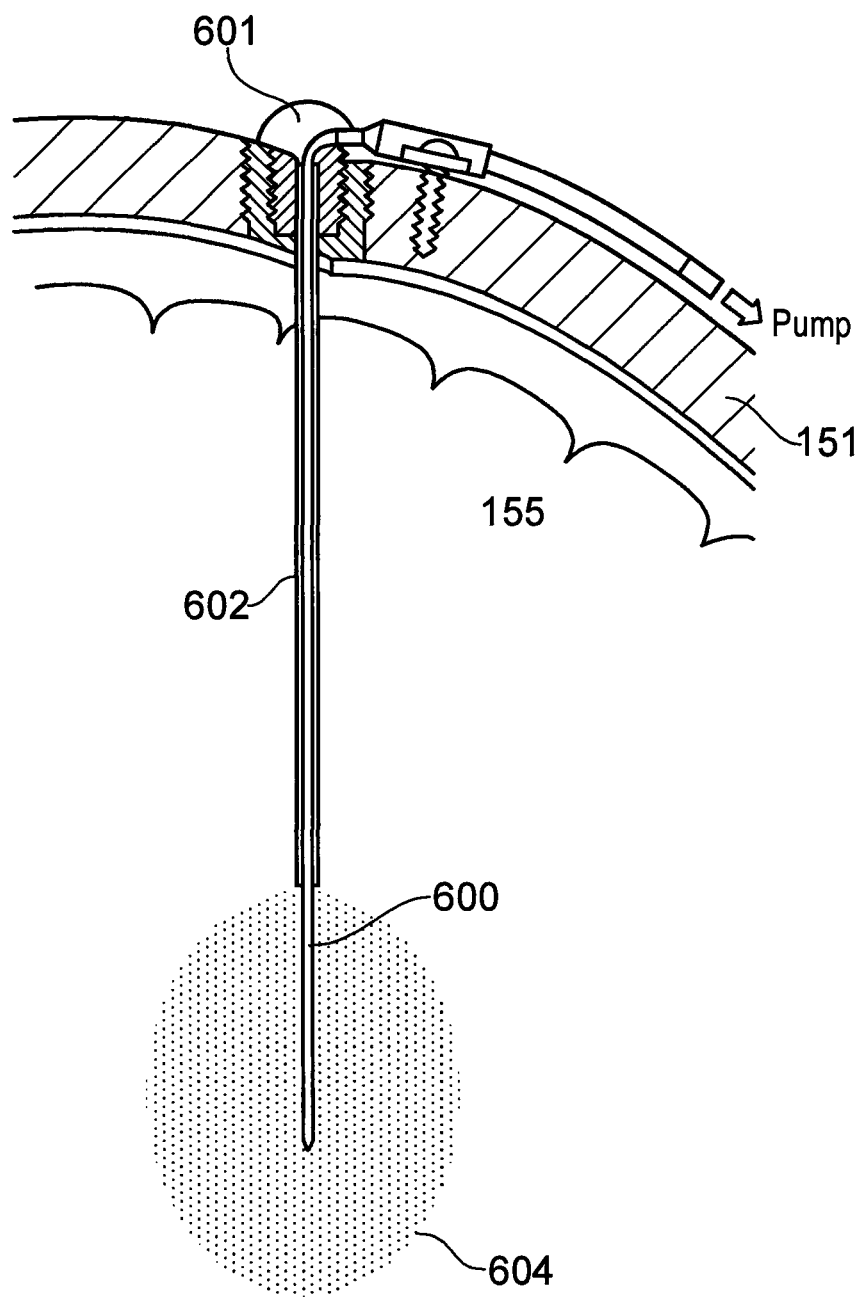
FIG. 10 is a cross-sectional view of an instrument implanted into the brain.

FIG. 10 shows an implantable instrument, in this instance a catheter 600 inserted through a guide tube 602 into the opening formed using the cranial drill system. The catheter 600 can then be used to deliver a drug to a target area 604. The stepped profile formed in the skull by the second drilling element receives the port 601, which has a corresponding profile.

Figure 11:
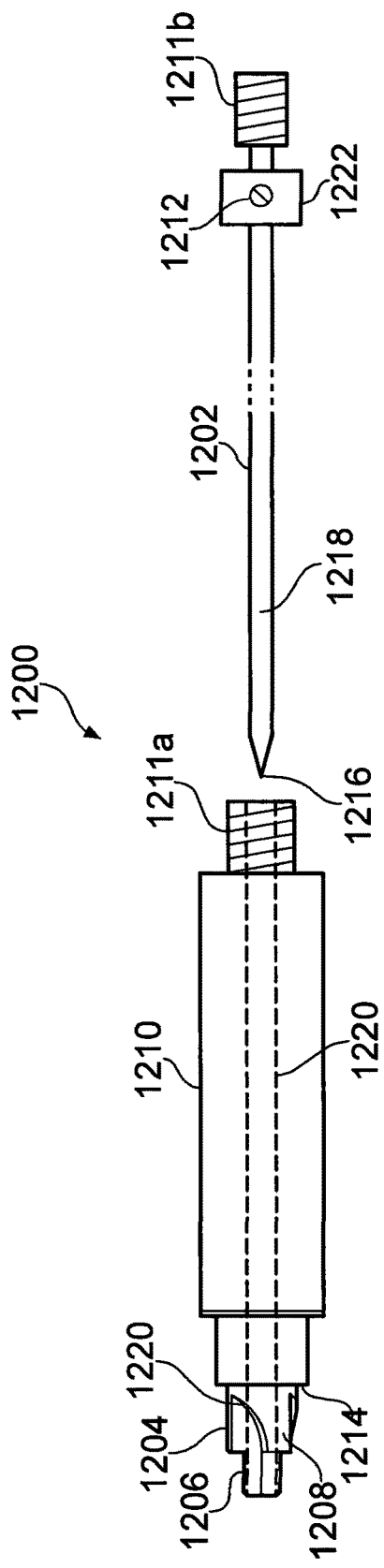
FIG. 11 shows a cranial drill system according to a further embodiment of the invention.
Figure 12A:
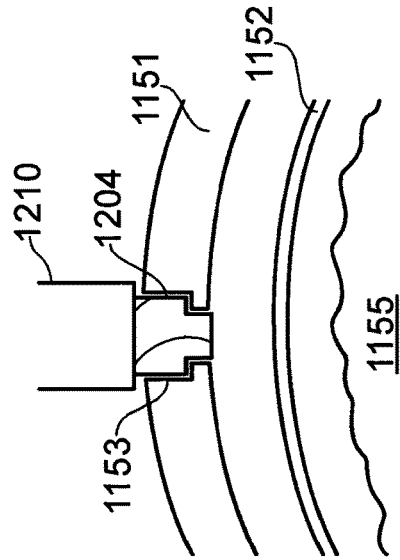
FIGS. 12A to 12D shows schematically a method of neurosurgery using the cranial drill system shown in FIG. 11.
Figure 12B:
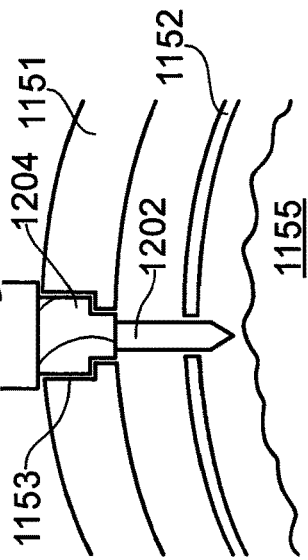
Figure 12C:
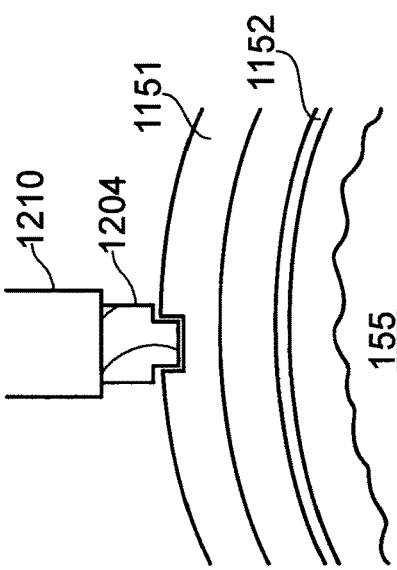
Figure 12D:
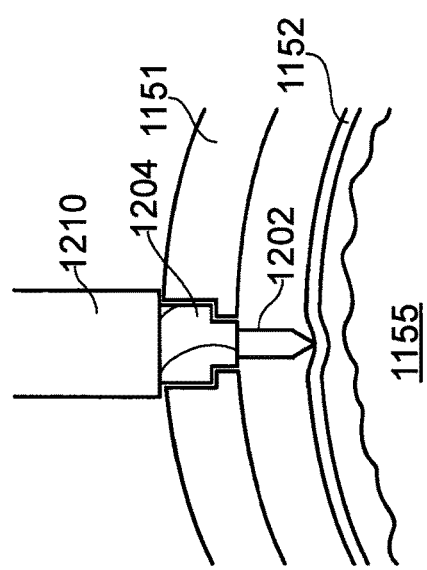

A further embodiment of the invention is shown in FIGS. 11 and 12A to 12D. This embodiment is similar to the embodiment shown in FIG. 3 and like reference numerals but in the series 1000 have been used for corresponding features. This embodiment differs from the embodiment shown in FIG. 3 in that the first drilling element 202 has been replaced with a spike 1202 for penetrating the dura 1152. The spike 1202 comprises a smooth shaft 1218 without flutes of a drill element and a point 1216. In use, a hole is drilled into the skull using drill element 1204 and then the passageway 1220 is used as a guide to guide the spike 1202 to the desired location above the dura 1152. The spike 1202 is then inserted further to pierce the dura, as shown in FIG. 12D. The spike 1202 may be removed before it enters the brain 1155, penetration of the brain achieved using other instruments.

Figure 13:
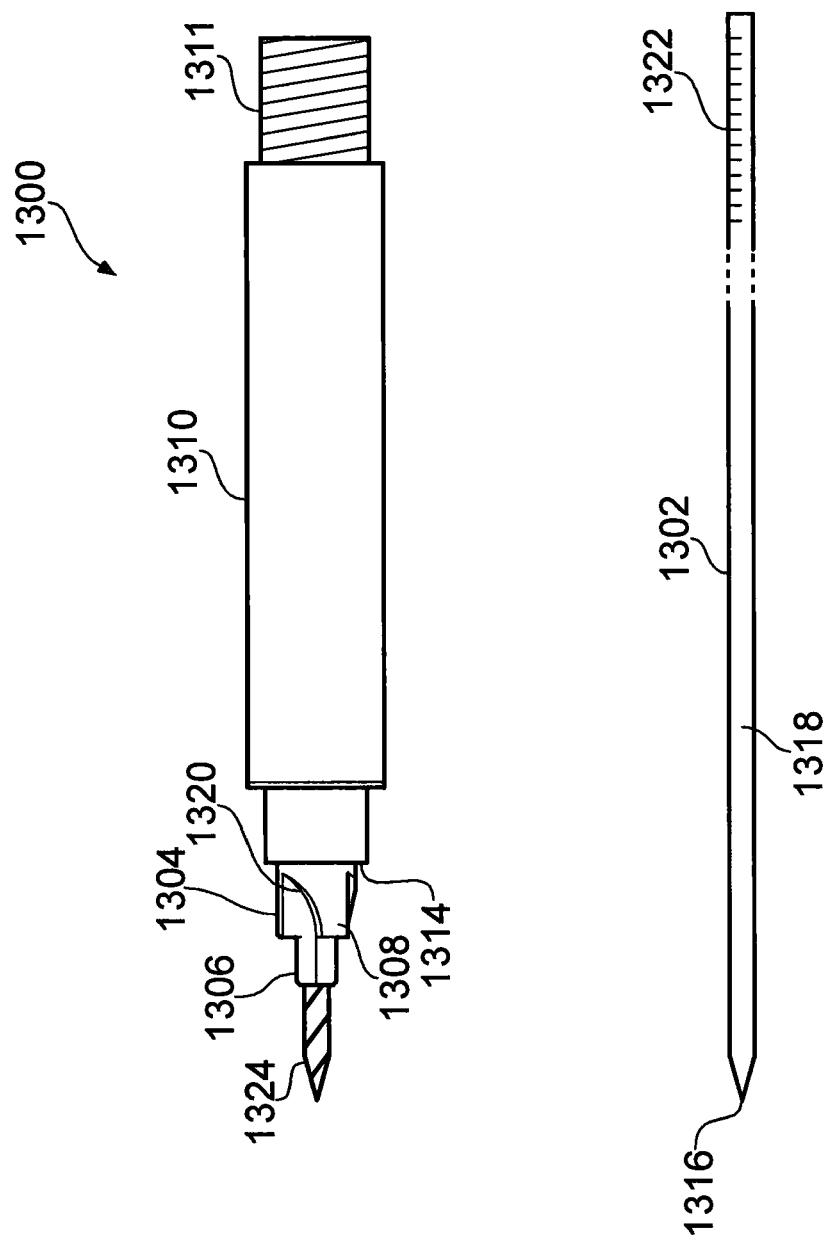
FIG. 13 shows a cranial drill system according to yet another embodiment of the invention.

FIG. 13 shows an arrangement similar to FIG. 5 but with the first drilling element 302 replaced with a spike 1302 for penetrating the dura. The spike 1302 is arranged to be a close fit in the pilot hole drilled using the pilot drill 1324 Such an arrangement may not have some of the benefits derived from drilling into the brain but may benefit from puncturing of the dura with the spike guided by a pilot hole formed in the skull.

Furthermore, in either of the embodiments shown in FIGS. 11 and 13, a spike for puncturing the dura may be provided in addition to the first drilling element. With such a system, the spike may be a close fit in the pilot hole and inserted into the pilot hole to puncture the dura. The spike is then removed and the first drill element inserted into the pilot hole to drill into the brain.

As a modification to the embodiment shown in FIG. 11, a separate guide element for guiding the spike may be provided. In such an embodiment, a drill element is provided for drilling a particular profile in the skull. The separate guide element comprises a portion having a profile corresponding to the profile of the hole formed using the drill element so that it can be located accurately in the hole through engagement with the hole. The spike is then inserted through the guide element to penetrate the dura.

It will be understood that various modifications and alterations can be made to the described embodiments without departing from the invention as defined herein.

The invention claimed is:

1. A kit comprising: a cranial drill system comprising:
at least one surgical drill element configured to drill into a skull and to form an opening in the skull, the opening having a narrower diameter portion and a wider diameter portion; and
a spike configured to penetrate a dura, the spike dimensioned to be a close fit in the narrower diameter portion of the opening such that lateral translational movement of a section of the spike is limited when the section of the spike is located in the narrower diameter portion of the opening; and an implantable instrument configured to locate within the opening formed using the cranial drill system, the implantable instrument comprising a port, wherein the cranial drill system is arranged to form the opening having a profile corresponding to a profile of the port.

2. A neurosurgical apparatus comprising:
a coordinate positioning apparatus configured to position surgical instruments relative to a skull; and
a kit according to claim 1.

3. The kit according to claim 1,
wherein the implantable instrument further comprises a guide tube, and
the port is located at a proximal end of the implantable instrument.

4. The kit according to claim 3, wherein the proximal end of the implantable instrument comprises a stepped profile.

5. The kit according to claim 4, wherein the stepped profile comprises a stepped profile of the port.

6. The kit according to claim 4, wherein the stepped profile comprises a step between the port and the guide tube.

7. A cranial drill system comprising:
a first drill element configured to drill into a skull;
a second drill element configured to drill into the skull; and
an element configured to penetrate at least one of a dura and a brain,
wherein the second drill element comprises a guide that, during drilling with the second drill element, is configured to extend into and is a close fit in an opening formed by the first drill element in the skull, and
the element configured to penetrate the at least one of the dura and the brain is arranged to be an interference fit in the opening formed in the skull.

8. A cranial drill system as claimed in claim 7, wherein the second drill element comprises a profile configured to form an opening in the skull having wider and narrower portions.

9. A cranial drill system as claimed in claim 8, wherein the opening in the skull formed by the second drill element comprises at least one stepped transition between the wider and narrower portions.

10. A cranial drill system as claimed in claim 7, further comprising a separate guide element configured to guide the element configured to penetrate the at least one of the dura and the brain, the separate guide element being locatable in the opening through engagement with the opening.

* * * * *